(12) United States Patent
Yang et al.

(10) Patent No.: US 7,790,375 B2
(45) Date of Patent: Sep. 7, 2010

(54) PRIMER FOR DETECTION OF HUMAN PAPILLOMAVIRUS

(75) Inventors: Joo-Sung Yang, Seoul (KR); Hyeran Cha, Seoul (KR)

(73) Assignee: Sungkyunkwan University, Seoul (KR)

( * ) Notice: Subject to any disclaimer, the term of this patent is extended or adjusted under 35 U.S.C. 154(b) by 0 days.

(21) Appl. No.: 10/581,649

(22) PCT Filed: Mar. 14, 2006

(86) PCT No.: PCT/KR2006/000915

§ 371 (c)(1),
(2), (4) Date: Nov. 2, 2007

(87) PCT Pub. No.: WO2006/098582

PCT Pub. Date: Sep. 21, 2006

(65) Prior Publication Data

US 2009/0017450 A1 Jan. 15, 2009

(30) Foreign Application Priority Data

Mar. 14, 2005 (KR) ............... 10-2005-0020863

(51) Int. Cl.
*C12Q 1/68* (2006.01)
(52) U.S. Cl. ............................................. 435/6
(58) Field of Classification Search ................. None
See application file for complete search history.

(56) References Cited

U.S. PATENT DOCUMENTS 6,582,908 B2 * 6/2003 Fodor et al. ............... 506/9

FOREIGN PATENT DOCUMENTS

| KR | 10-2004-0036318 | | 4/2004 |
| KR | 10-2004-0078506 | | 9/2004 |
| KR | 10-2004-083674 | | 10/2004 |
| WO | WO01 68915 A1 | | 9/2001 |
| WO | WO 03019143 A3 | | 3/2003 |
| WO | WO03027323 A1 | | 4/2003 |
| WO | WO 03076667 A1 | * | 9/2003 |

OTHER PUBLICATIONS

Lowe et al. (Nucleic Acids Research, vol. 18, No. 7, p. 1757-1761, 1990).*
NCBI (Accession No. M14119, Jun. 2, 1994).*
NCBI (Accession No. K02718, Mar. 18, 1994).*
NCBI (Accession No. AY262282, Apr. 28, 2003).*
NCBI (Accession No. J043553, Mar. 18, 1994).*
Brule et al, "Rapid Detection of Human Papillomavirus in Cervical Scrapes by Combined General Primer-Mediated and Type Specific Polymerase Chain Reaction," Journal of Clinical Microbiology (1990) V. 28, pp. 2739-2743.
Dahlgren et al, "Human Papilloma Virus is More Common in Base of Tongue Than in Mobile Tongue Cancer and is a Favorable Prognostic Factor in Base of Tongue Cancer Patients" Int. J. Cancer, v 112, pp. 1015-1019 (2004).
Karlsen et al, "Use of Multiple PCR Primer Sets for Optimal Detection of Human Papillomavirus," Journal of Clinical Microbiology, (1996) vol. 34 pp. 2095-2100.
Snijders et al, "Prevalence of Mucostropic Human Papillomaviruses in Squamous-Cell Carcinomas of the Head and Neck," Int. J.Cancer (1996) vol. 66 pp. 464-469.
Burel et al, "Detection of Human Papillomavirus in Squamous Intraepithelial Lesions by Consensus and Type-Specific Polymerase Chain Reaction," European Journal of Obstetrics & Gynecology, (1993) vol. 52 pp. 193-200.
Lee et al, "Human Papillomavirus Infection in Non-Neoplastic Uterine Cervical Disease in Hong Kong," British Journal of Biomedical Science, (2001) vol. 58, pp. 83-91.
Tenti et al, "Perinatal Transmission of Human Papillomarvirus From Gravidas With Latent Infections," Obstetrics & Gynecology, (1999) vol. 93, pp. 475.
UK IPO Office Action Issued in Corresponding UK Application No. GB0610705.6; Applicant: Sungkyunkwan University; Date of Report: Oct. 22, 2008 (2 PGS).
Brown et al, "HPV Subtype Analysis in Lower Gential Tract Neoplasms of Female Renal Transplant Recipients," Gynecological Oncology, (2000) vol. 70 pp. 220-224.
English Translation of Abstract Only, KR Patent Application Publication No. KR10-2004-0036318; Applicant: Genomictree Inc.; Published: Apr. 30, 2004 (1 pg.).
English Translation of Abstract Only, KR Patent Application Publication No. KR10-2004-0078506; Applicant: Biomedlab Co., Ltd.; Published: Sep. 10, 2004 (2 pgs.).
English Translation of Abstract Only, KR Patent Application Publication No. KR10-2004-083674; Applicant: Biocore Co., Ltd.; Published: Oct. 6, 2004 (2 pgs.).
Pfaller, Michael A.; "Molecular Approaches to Diagnosing and Managing Infectious Diseases: Practicality and Costs"; Emerging Infectious Diseases; vol. 7, No. 2, Mar.-Apr. 2001, pp. 312-318.

* cited by examiner

*Primary Examiner*—Christopher M. Babic
(74) *Attorney, Agent, or Firm*—Casimir Jones, S.C.

(57) ABSTRACT

Disclosed are primers specific to the genome of HPV genotypes 11, 16, 18 and 31. Also disclosed are a kit for detecting the HPV genome comprising the primers and a method of detecting the HPV genome using the primers.

1 Claim, 12 Drawing Sheets

Fig. 4 a. Time point : 0 week b. Time point : 3 week

Type11 & Type16

Type18 & Type31

PRIMER FOR DETECTION OF HUMAN PAPILLOMAVIRUS

TECHNICAL FIELD

The present invention relates to primers specific to the genome of human papillomavirus (hereinafter, referred to as "HPV"), a kit for detecting the HPV genome comprising the primers, and a method of detecting the HPV genome using the primers.

BACKGROUND ART

HPV is a double-stranded DNA virus whose circular genome is approximately 8 kb long. HPV inhabits the vagina, and the infection thereof is hard to treat and is not easily made to disappear. HPV infects the epithelial cells of other mammals as well as humans, and generally induces warts, and sometimes malignant tumors, at the site of infection. HPV is detected in over 90% of condyloma accuminata cases (enlarged warts having a cauliflower-like appearance around the genitals or the anus) and almost 100% of cervical cancer cases. In particular, cervical cancer accounts for 22.1% of all cancers found in women in Korea, and is the second leading cause of cancer death among women.

Thus, establishing a method of effectively detecting HPV, which causes cervical cancer, is important for the diagnosis, prophylaxis and therapy of the disease. Also, HPV needs to be effectively detected to evaluate the efficacy and toxicity of a vaccine against HPV after vaccination.

A nucleic acid-based test for diagnosing an infectious disease employs a standard method of isolating nucleic acids from individuals and clinical materials. Since target DNA or RNA is present in clinical specimens in small amounts, several major techniques used in diagnostic laboratories are based on signal amplification and target amplification. These methods aid detection, are useful in the identification of individuals without culture, and contribute to the treatment as well as diagnosis of infectious diseases. PCR, which is a nucleic acid amplification technique (NAT), is widely used because it enables the selective amplification of specific targets, present in low concentrations, to detectable levels. In addition to the qualitative detection of viruses, quantitative determination of viral load in, clinical specimens is now realized to be of great importance with respect to the diagnosis, prognosis, and therapeutic monitoring of HPV infection (Pfaller M. A, Emer. Infect. Dis. 7, 2, 2001).

The genome of all types of HPV is divided into two major regions: early and late regions. The early region of about 4.5 kb codes for genes which are associated with functions including viral DNA replication (E1), induction or suppression of the action of DNA encoding a protein inducing malignant transformation of host cells (E2), synthesis of proteins responsible for the growth of host cells and viruses (E4), stimulation of the activity of epidermal growth factor (EGF) and colony stimulator factor (CSF) receptors (E5), and malignant transformation through permanent survival of cells, activation of oncogenes and inactivation of tumor suppressor genes (E7). In particular, the oncogenic E6 and E7 proteins, which are expressed after HPV infects the epithelial cells of a host, bind to tumor suppressor proteins of host cells, p53 and pRB, respectively, thereby inhibiting the function of the tumor suppressor proteins, leading to the transformation of infected cells, resulting in the development of tumors. The late region of 2.5 kb comprises genes coding for viral major (L1) and minor (L2) capsid proteins and a non-coding region of 1 kb, which is called the long control region (LCR) that regulates the transcription and translation of the two late genes.

With recent rapid advances in molecular biological techniques, the genetic structure of HPV has been identified, revealing genomic sequences of many genotypes of HPV. HPV is classified according to the difference in DNA sequences of E6, E7 and L1 open reading frames (ORFs). When the nucleotide sequences of the ORFs differ by more than 10%, an HPV is assigned a new genotype. HPV subtypes differ by 2% to 10%, and HPV variants differ by less than 2%.

In order to specifically detect high risk HPV types 16, 18 and 31 and a low risk HPV type 11 among a large number of HPV genotypes, which are detected in tissues of cervical cancer and carcinoma in situ, respectively, the present inventors intended to detect a gene specific to each genotype of these viruses, and selected the L1 gene as such a gene.

In order to specifically detect the HPV L1 gene, the present inventors determined the sequences of L1 genes of the HPV types 11, 16, 18 and 31, which are specifically found in Koreans, and constructed primers capable of specifically binding to the L1 gene of each HPV type. The present inventors found that when PCR was performed with the primers, each HPV genotype can be specifically detected and can be precisely quantified down to very low amounts, thereby leading to the present invention.

DISCLOSURE OF THE INVENTION

It is therefore an object of the present invention to provide a primer pair selected from among pairs of primers capable of complementarily binding to the genome of human papillomavirus (HPV) and having nucleotide sequences represented by SEQ ID Nos. 1 and 2, SEQ ID Nos. 3 and 4, SEQ ID Nos. 5 and 6, and SEQ ID Nos. 7 and 8.

It is another object of the present invention to provide a method of detecting the HPV genome, which is based on performing a polymerase chain reaction (PCR) for DNA contained in a biological sample using one or more primer pairs selected from among pairs of primers capable of complementarily binding to the HPV genome and having nucleotide sequences represented by SEQ ID Nos. 1 and 2, SEQ ID Nos. 3 and 4, SEQ ID Nos. 5 and 6, and SEQ ID Nos. 7 and 8.

It is a further object of the present invention to provide a kit for detecting the HPV genome, comprising one or more primer pairs selected from among pairs of primers capable of complementarily binding to the HPV genome and having nucleotide sequences represented by SEQ ID Nos. 1 and 2, SEQ ID Nos. 3 and 4, SEQ ID Nos. 5 and 6, and SEQ ID Nos. 7 and 8.

BRIEF DESCRIPTION OF THE DRAWINGS

The above and other objects, features and other advantages of the present invention will be more clearly understood from the following detailed description taken in conjunction with the accompanying drawings, in which:

FIG. 2 is an alignment of HPV 16 L1 sequences;

FIG. 3 is an alignment of HPV 31 L1 sequences;

FIG. 4 is an alignment of HPV 11 L1 sequences;

FIG. 7A shows measured band intensity of separated PCR products on agarose gel. FIG. 7B shows band intensity measured using the software Quantity One (Bio-Rad), and the relationship between band intensity and the number of plasmid copies;

BEST MODE FOR CARRYING OUT THE INVENTION

In one aspect, the present invention relates to primers capable of complementarily binding to the HPV genome.

In a detailed aspect, the present invention relates to a primer pair selected from among pairs of primers capable of complementarily binding to the HPV genome and having the nucleotide sequences represented by SEQ ID Nos. 1 and 2, SEQ ID Nos. 3 and 4, SEQ ID Nos. 5 and 6, and SEQ ID Nos. 7 and 8.

Figure 2:
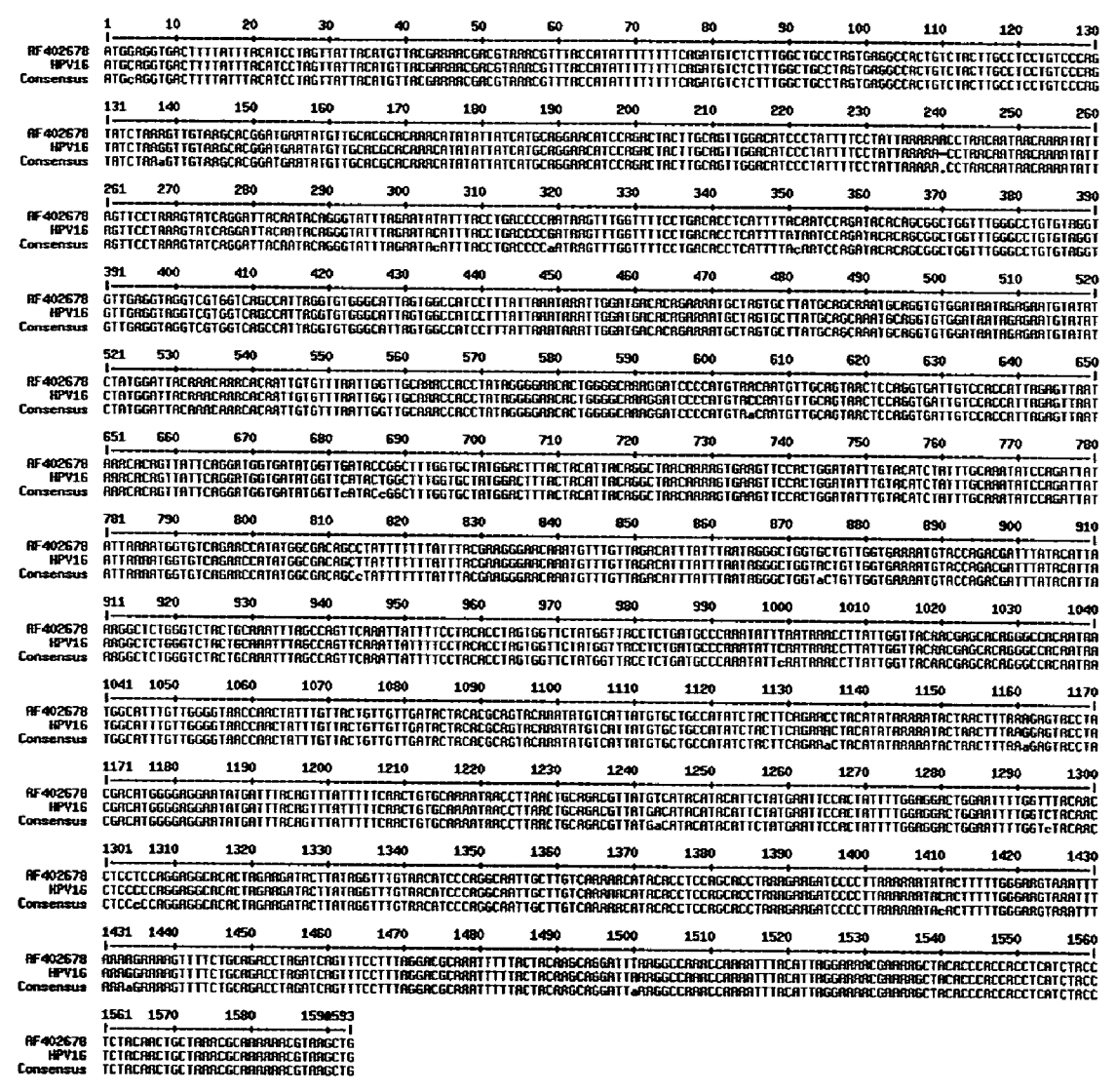
Figure 3:
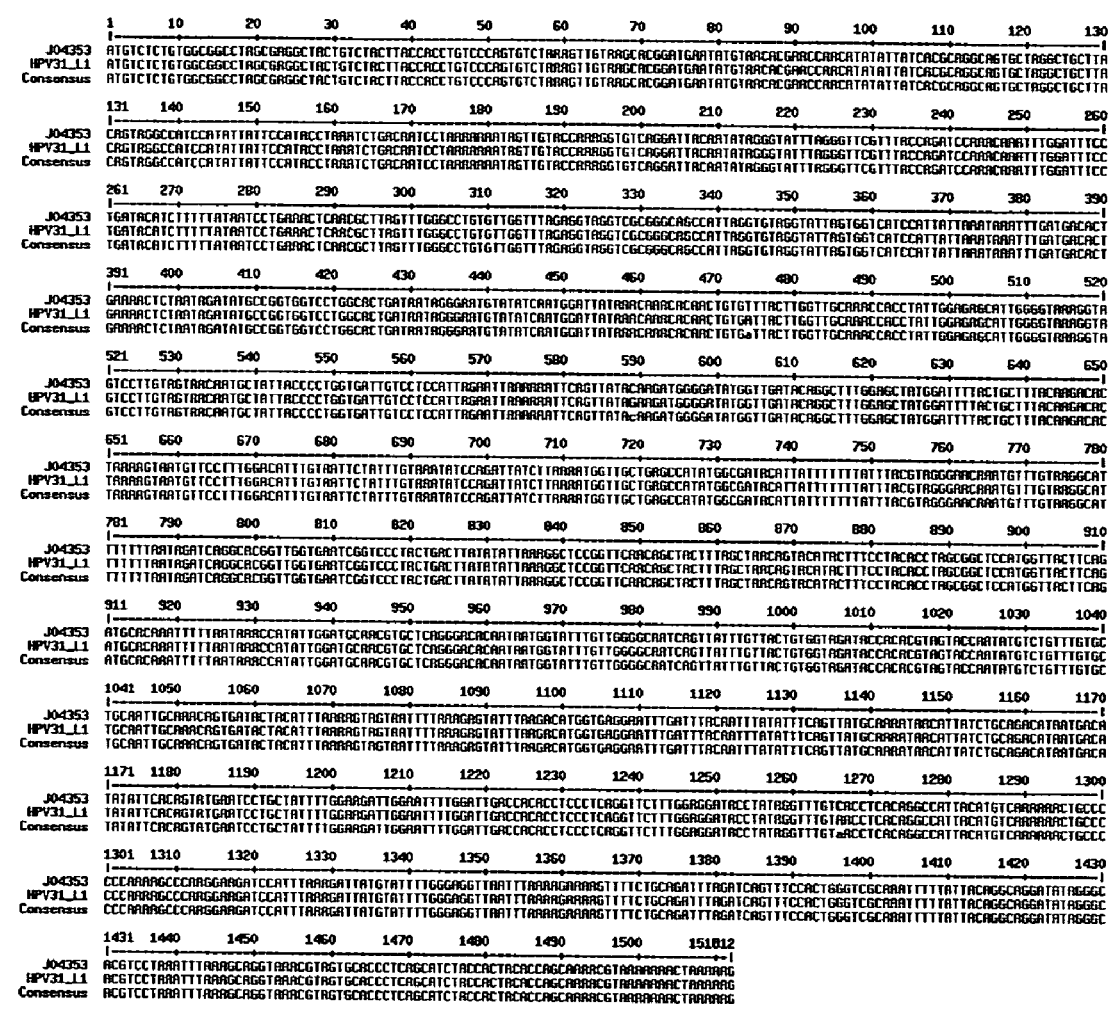
Figure 4:
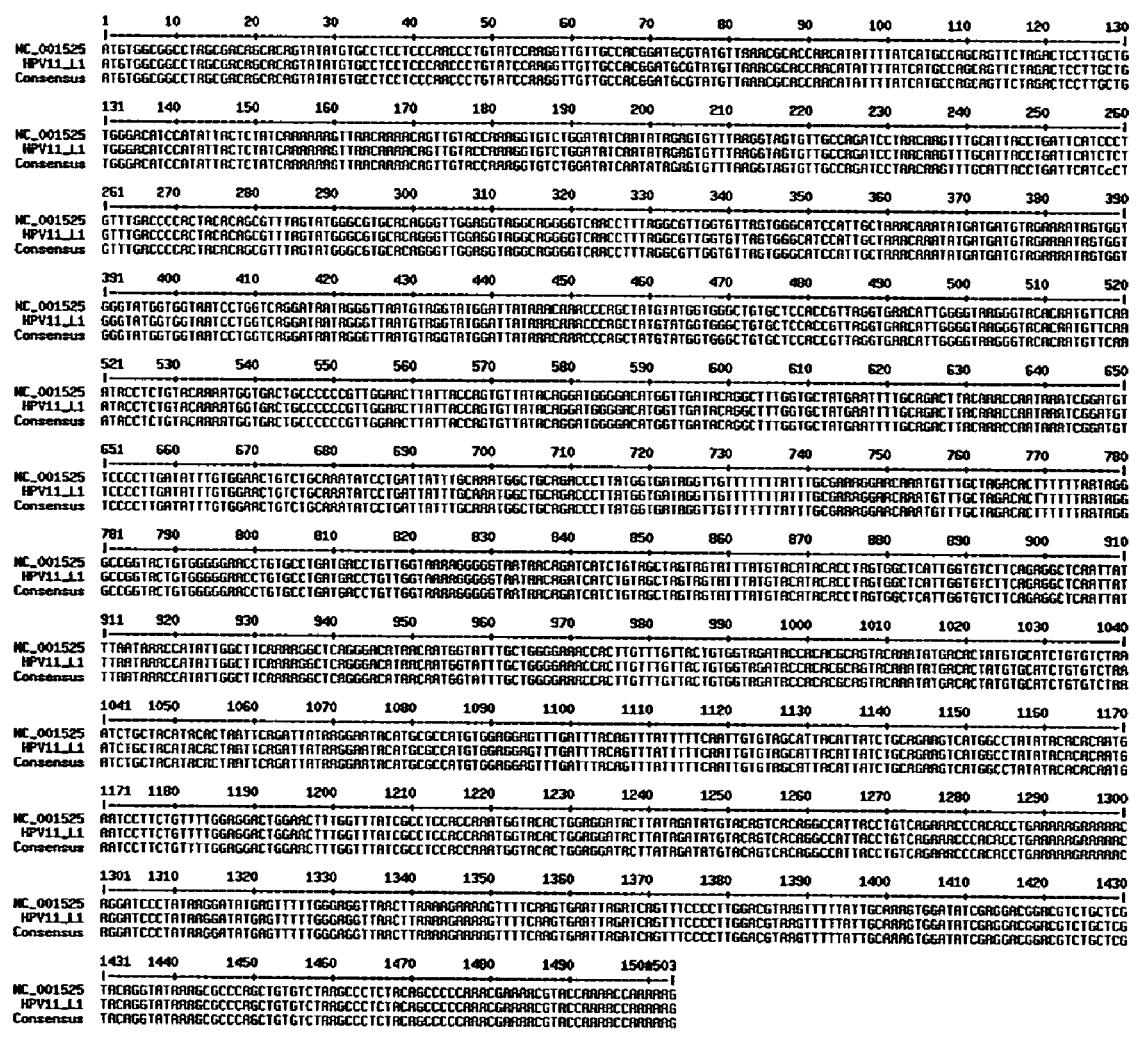
Figure 5:
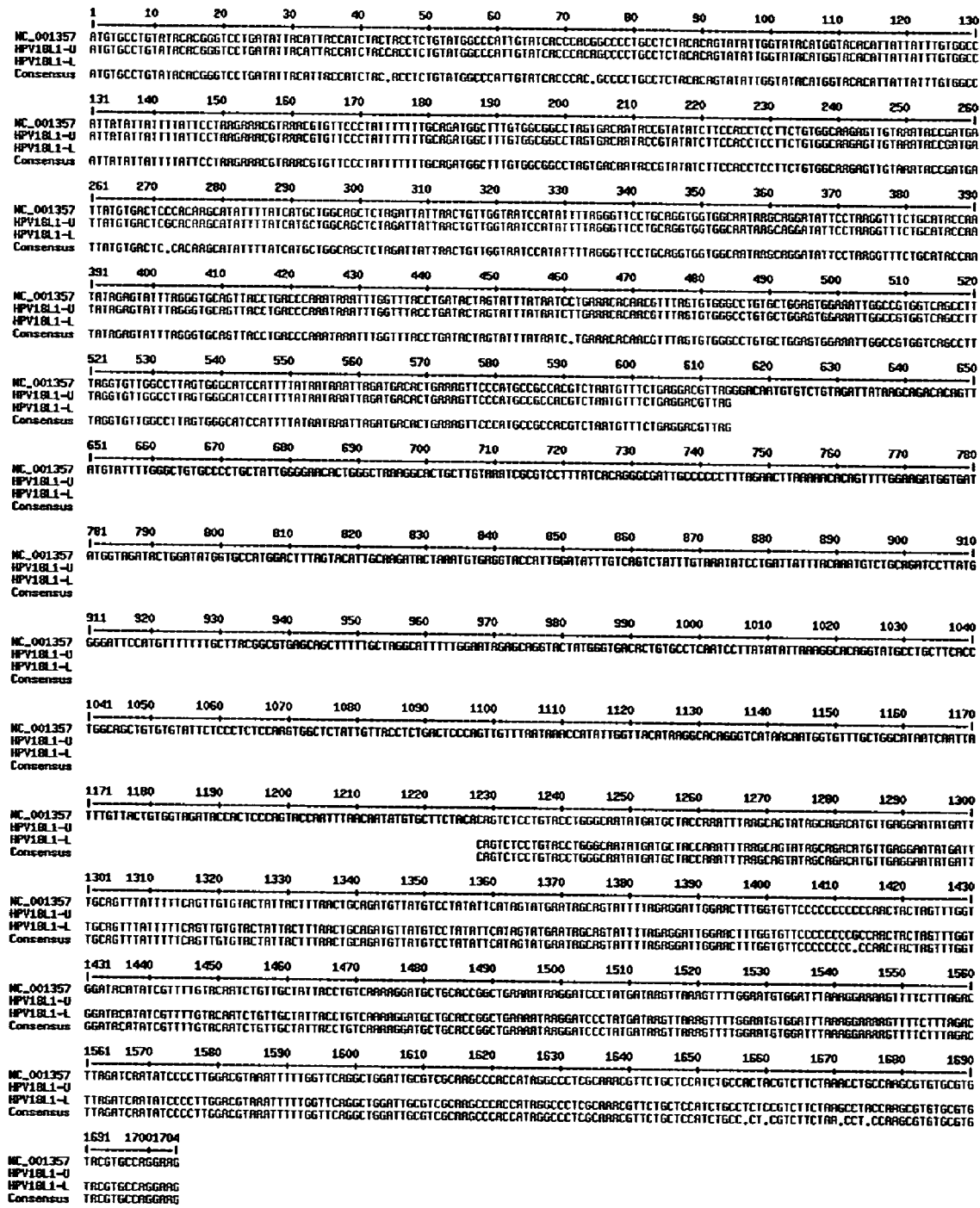
FIG. 5 is an alignment of HPV 18 L1 sequences.

The term "primer", as used herein, refers to a short nucleic acid sequence having a free 3' hydroxyl group, which is able to undergo base-pairing interaction with a complementary template and serves as a starting point for replicating the template strand. A primer is able to initiate DNA synthesis in the presence of a reagent for polymerization and four different nucleoside triphosphates in suitable buffers and at a suitable temperature. With respect to the objects of the present invention, primers specifically amplify a specific region of the L1 gene of HPV 16, described in FIG. 2, HPV 31, described in FIG. 3, HPV 11, described in FIG. 4, and HPV 18, described in FIG. 5. Thus, the primers of the present invention consist of a pair of sense and antisense primers having a sequence of 7 to 50 nucleotides, and more preferably 10 to 30 nucleotides, the sequence capable of complementarily binding to the aforementioned HPV L1 gene. In detail, a specific region of the HPV L1 gene may be specifically amplified with a pair of primers having the nucleotide sequences of SEQ ID Nos. 1 and 2 for HPV 11, a pair of primers having the nucleotide sequences of SEQ ID Nos. 3 and 4 for HPV 16, a pair of primers having the nucleotide sequences of SEQ ID Nos. 5 and 6 for HPV 18, and a pair of primers having the nucleotide sequences of SEQ ID Nos. 7 and 8 for HPV 31.

The primers of the present invention may be chemically synthesized using a phosphoramidite solid support method or other widely known methods. These nucleic acid sequences may also be modified using any means known in the art. Non-limiting examples of such modifications include methylation, capsulation, replacement of one or more native nucleotides with analogues thereof, and inter-nucleotide modifications, for example, modifications to uncharged conjugates (e.g., methyl phosphonate, phosphotriester, phosphoroamidate, carbamate, etc.) or charged conjugates (e.g., phosphorothioate, phosphorodithioate, etc.). Nucleic acids may contain one or more additionally covalent-bonded residues, which are exemplified by proteins (e.g., nucleases, toxins, antibodies, signal peptides, poly-L-lysine, etc.), intercalating agents (e.g., acridine, psoralene, etc.), chelating agents (e.g., metals, radioactive metals, iron, oxidative metals, etc.), and alkylating agents. The nucleic acid sequences of the present invention may also be altered using a label capable of directly or indirectly supplying a detectable signal. Examples of such a label include radioisotopes, fluorescent molecules, and biotin.

When PCR was performed with the primers provided in the present invention, which have the nucleotide sequences of SEQ ID Nos. 1 and 2, SEQ ID Nos. 3 and 4, SEQ ID Nos. 5 and 6, and SEQ ID Nos. 7 and 8, the primers were found to be able to specifically detect each of the four different HPV genotypes and to be sensitive enough to amplify as few as 62.5 copies of a plasmid.

Thus, the present primers may be useful in the detection of HPV infections, the identification of infective HPV genotypes, the epidemiological evaluation of HPV, the effectiveness and toxicity of developed HPV vaccines, and the like.

In another aspect, the present invention provides a method of detecting the HPV genome, which is based on performing a polymerase chain reaction (PCR) for DNA contained in a biological sample using one or more primer pairs selected from among pairs of primers capable of complementarily binding to the HPV genome and having the nucleotide sequences represented by SEQ ID Nos. 1 and 2, SEQ ID Nos. 3 and 4, SEQ ID Nos. 5 and 6, and SEQ ID Nos. 7 and 8.

The term "biological sample", as used herein, includes, but is not limited to, samples, such as tissues, cells, whole blood, sera, plasma, saliva, sputa, cerebrospinal fluid, urine, or the like, of individuals infected with HPV or suspected of being infected with HPV, or individuals vaccinated with a HPV vaccine.

A method for identifying the presence and genotype of HPV is particularly not limited as long as it employs the aforementioned primers. Examples of such methods include direct identification of HPV DNA using a primer of a specific strand as a probe, Southern blotting, dot blotting, and filter in situ hybridization (FISH). Alternative methods include a method based on amplifying HPV DNA using a pair of primers, genotype-specific polymerase chain reaction (PCR), and general-primer PCR. PCR is most preferred.

The term "polymerase chain reaction (PCR)", as used herein, is a representative nucleic acid amplification technique (NAT), which enzymatically amplifies a specific DNA region of interest in vitro. The PCR method, which was developed in 1985 by Mullis et al., can amplify any segment of a DNA molecule if its boundary sequences are known. PCR basically consists of three major steps: denaturation, annealing and extension. A specific DNA sequence is amplified while these three steps are repeated. In the first step (denaturation) of PCR, a double-stranded template DNA is denatured into two single strands. In the second step (annealing), primers anneal with the two kinds of single-stranded DNA, in which a sequence desired to be amplified is interposed between the primer binding regions. In the third step (extension), a heat-resistant DNA polymerase extends the primers and synthesizes the complementary strand of the target sequence. This cycle is repeated 25 to 30 times.

Primers are the most important factor determining the reliability of PCR results. Some primer sequences can give rise to non-specific amplification, leading to false results. In this regard, the present invention provides reliable primer pairs. The performance of PCR with the primer pairs of the present invention enables accurate detection of HPV genotypes and sensitive quantitative analysis of very small amounts. Also, when PCR is carried out with the primer pairs of the present invention, consistent results are obtained upon repeated PCR performance. That is, since the primer pairs of the present invention are highly valid and reliable, the results obtained with the present primer pairs are highly reliable.

In a preferred aspect, the present invention provides a method of detecting the HPV 11 L1 gene using a pair of primers having the nucleotide sequences of SEQ ID Nos. 1 and 2.

In another preferred aspect, the present invention provides a method of detecting the HPV 16 L1 gene using a pair of primers having the nucleotide sequences of SEQ ID Nos. 3 and 4.

In a further preferred aspect, the present invention provides a method of detecting the HPV 18 L1 gene using a pair of primers having the nucleotide sequences of SEQ ID Nos. 5 and 6.

In yet another preferred aspect, the present invention provides a method of detecting the HPV 31 L1 gene using a pair of primers having the nucleotide sequences of SEQ ID Nos. 7 and 8.

A PCR for amplifying an HPV gene, in detail the L1 gene, using the primers of the present invention may be carried out through an ordinary PCR method. Also, conditions including time, temperature and cycle number, under which denaturation, annealing and extension reactions are allowed to occur, may vary. In the present invention, PCR conditions included 35 cycles of denaturation at 94° C. for 1 min, annealing at 51° C. for 1 min, and extension at 72° C. for 1 min or 1 min 30 sec.

In a further aspect, the present invention provides a kit for detecting the HPV genome, comprising one or more primer pairs selected from among pairs of primers capable of complementarily binding to the HPV genome and having the nucleotide sequences represented by SEQ ID Nos. 1 and 2, SEQ ID Nos. 3 and 4, SEQ ID Nos. 5 and 6, and SEQ ID Nos. 7 and 8.

In addition to the primer pairs, the detection kit of the present invention is composed of one or more different compositions, solutions or instruments, which are suitable for analysis methods. Preferably, the kit of the present invention includes the following constituents: a container containing detection primers; amplification reaction tubes or other suitable containers; reaction buffer (pH and magnesium concentration of which may vary); dNTPs; an enzyme such as Taq-polymerase; RNase; and sterile water. More preferably, the kit may further include a plasmid carrying an HPV gene as a positive control in order to realize quantitative analysis. Such a plasmid may be one or more selected from among pGEM-HPV11 L1, pGEM-HPV16 L1, pGEM-HPV18 L1, and pGEM-HPV31 L1, which will be described in the following examples.

A better understanding of the present invention may be obtained through the following examples which are set forth to illustrate, but are not to be construed as the limit of the present invention.

EXAMPLE 1

Construction of Recombinant HPV L1 Plasmids (Standard DNA)

PCR primers specific to low risk HPV 11 and high risk HPV 16, 18 and 31 were designed based on major protein (HPV L1) sequences of the different genotypes of HPV, which are deposited in GenBank. In order to obtain HPV genotypes commonly found in Korean, tissues of Korean cervical cancer patients were obtained from clinical hospitals, and genomic DNA as an HPV genome source was extracted from the tissues. Biological tissue samples were paraffin sections or biopsy samples prepared for pathological examination. PCR was carried out using the extracted genomic DNA with primers having the nucleotide sequences of SEQ ID Nos. 9 to 16, which are listed in Table 1, below. As a result, PCR products of about 1.6 kb were obtained.

TABLE 1

Primer sequences against the HPV L1 gene for the preparation of national (Korean) standard DNA

| HPV genotype | PCR fragment length | | PCR primer sequence |
|---|---|---|---|
| HPV 16 | 1596 bp | Sense | 5'-GCCCCC<u>AAGCTT</u>GCCGCCACCATG CAGGTGACTTTTATTTACATCC-3' (SEQ ID No. 9) |
| | | Anti-sense | 5'-ATCGGG<u>CTCGAG</u>CAGCTTACGTTT TTTGCGTTTAGC-3' (SEQ ID No. 10) |
| HPV 18 | 1707 bp | Sense | 5'-GCCCCC<u>AAGCTT</u>GCCGCCACCATG TGCCTGTATACACGG-3' (SEQ ID No. 11) |
| | | Anti-sense | 5'-ATCGGG<u>GAATTC</u>CTTCCTGGCACG TACACGCACACG-3' (SEQ ID No. 12) |
| HPV 31 | 1515 bp | Sense | 5'-GCCCCC<u>AAGCTT</u>GCCGCCACCATG TCTCTGTGGCGGCCTAGC-3' (SEQ ID No. 13) |
| | | Anti-sense | 5'-ATCGGG<u>GAATTC</u>CTTTTTAGTTTT TTTACGTTTTGCTGGTGTAGTGG-3' (SEQ ID No. 14) |
| HPV 11 | 1506 bp | Sense | 5'-GCCCCC<u>AAGCTT</u>GCCGCCACCATG TGGCGGCCTAGCGACAGC-3' (SEQ ID No. 15) |
| | | Anti-sense | 5'-ATCGGG<u>GAATTC</u>CTTTTTGGTTTT GGTACGTTTTCGTTTGGG-3' (SEQ ID No. 16) |

Figure 1:
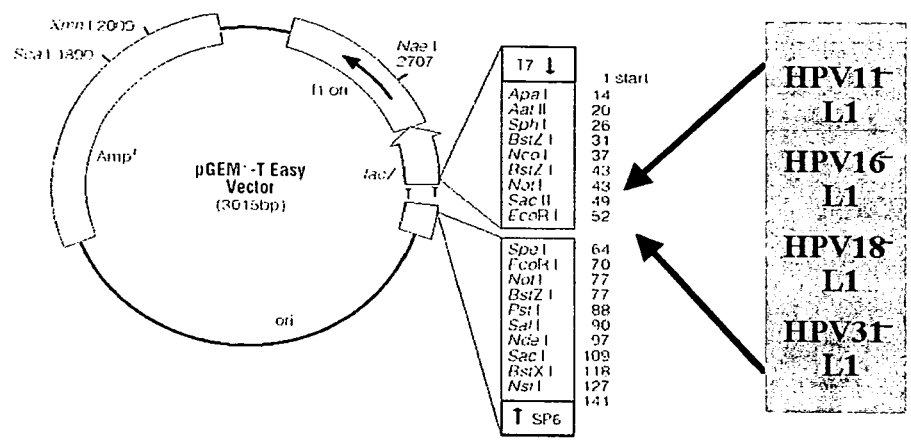
FIG. 1 schematically represents the construction of recombinant plasmids constructed with amplified L1 genes of HPV genotypes 11, 16, 18 and 31 (A), and also shows the results of restriction enzyme mapping of the recombinant plasmids (B)
Figure 1:
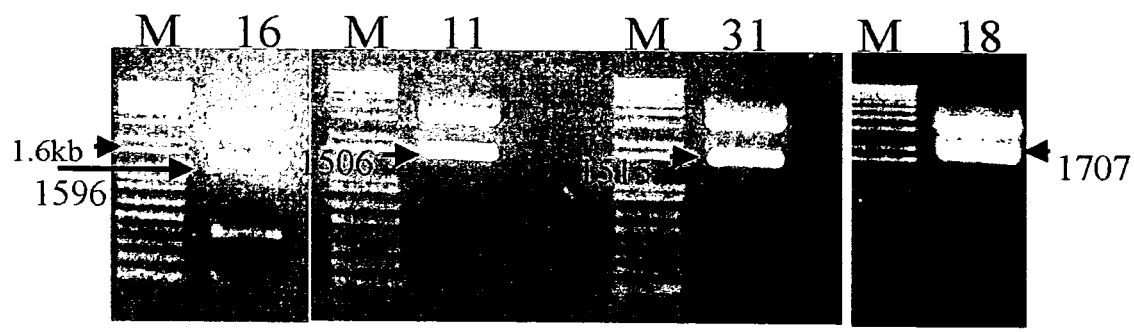

PCR was carried out under the following conditions. PCR was carried out using the DNA samples extracted from tissues from patients as templates with 2.5 mM dNTP, reaction buffer, primer pairs (20 pmol) listed in Table 1, and SuperTaq Plus. According to the optimal annealing temperature of primers, a cycle of denaturation at 94° C. for 1 min, annealing at Ta for 1 min, and extension at 72° C. for 1 min 30 sec was repeated thirty five times, followed by final extension at 72° C. for 10 min. Each PCR product was cloned into pGEM-T-Easy vector (Promega, USA) and transformed into E. coli DH5α. Plasmid DNA was then isolated and digested with EcoRI to determine whether the PCR product was successfully inserted (FIG. 1).

The nucleotide sequences of the PCR products were determined and compared with previously known nucleotide sequences coding for the L1 protein of HPV genotypes. HPV 16 was compared with AF402678, HPV 31 with J04353, HPV 11 with NC_001525, and HPV 18 with NC_001357. As a result, the nucleotide sequences coding for the L1 protein of the four HPV genotypes, which were identified according to the procedure described above, were found to be highly similar to the conventionally known nucleotide sequences coding for L1 proteins of the HPV genotypes.

EXAMPLE 2

Large Preparation and Quantification of the Recombinant HPV L1 Plasmids

*E. coli* cells transformed with the recombinant HPV L1 plasmids prepared in Example 1 were inoculated in 10 ml of LB medium supplemented with ampicillin, and grown in a shaking incubator at 37° C. overnight. Plasmid DNA was then isolated using an alkaline lysis method, and precisely quantified using a spectrophotometer. The plasmid copy number was calculated according to Equation 1, below.

Copy number of 1 kb fragment=(1000 bp×660 g/mole)/(6.023×10$^{23}$ molecules)=1×10$^{-18}$ g (1 fg) [Equation 1]

Equation 1 means the following. One copy of a 1 kb (1000 bp) plasmid weighs 1×10$^{-18}$ g (1 fg), and one gram of 1 kb plasmid DNA contains 10$^{18}$ copies of the plasmid.

Using Equation 1, the number of copies of each of different HPV genotype plasmids was calculated, and a plasmid solution having 2000 copies was serially diluted two-fold, thereby yielding 10-μl solutions containing 2000, 1000, 500, 250, 125 and 62.5 copies of the plasmids.

EXAMPLE 3

Figure 6:
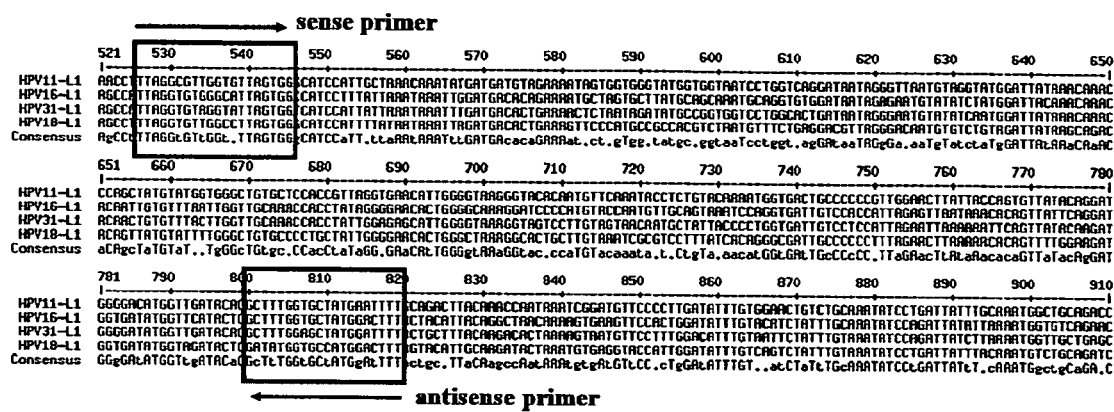
FIG. 6 is a multiple alignment of nucleotide sequences of L1 genes of HPV genotypes 11, 16, 18 and 31 and the consensus L1 sequence.

Evaluation of the Sensitivity of Specific Primers Using the Recombinant HPV L1 Plasmids Using the 10 μl plasmid solutions containing 2000, 1000, 500, 250, 125 and 62.5 copies, prepared in Example 2, PCR was carried out. As a result, PCR primers displayed sensitivity in a manner dependent on the number of plasmid copies (indicating that the 10 μl DNA solutions respectively contained 2000, 1000, 500, 250, 125 and 62.5 copies of the plasmids). Referring to FIG. 6, PCR primers represented by SEQ ID Nos. 1 to 8 (Table 2) were determined.

TABLE 2

Primers for detecting the HPV L1 gene

| Genotype | Sense primer | Anti-sense primer |
|---|---|---|
| HPV 11 | TTAGGCGTTGGTGTTAGTGG (SEQ ID No. 1) | AAAATTCATAGCACCAAAGC (SEQ ID No. 2) |
| HPV 16 | TTAGGTGTGGGCATTAGTGG (SEQ ID No. 3) | AAAGTCCATAGCACCAAAGC (SEQ ID No. 4) |
| HPV 18 | TTAGGTGTTGGCCTTAGTGG (SEQ ID No. 5) | AAAGTCCATGGCACCATATC (SEQ ID No. 6) |
| HPV 31 | TTAGGTGTAGGTATTAGTGG (SEQ ID No. 7) | AAAATCCATAGCTCCAAAGC (SEQ ID No. 8) |

Figure 7:
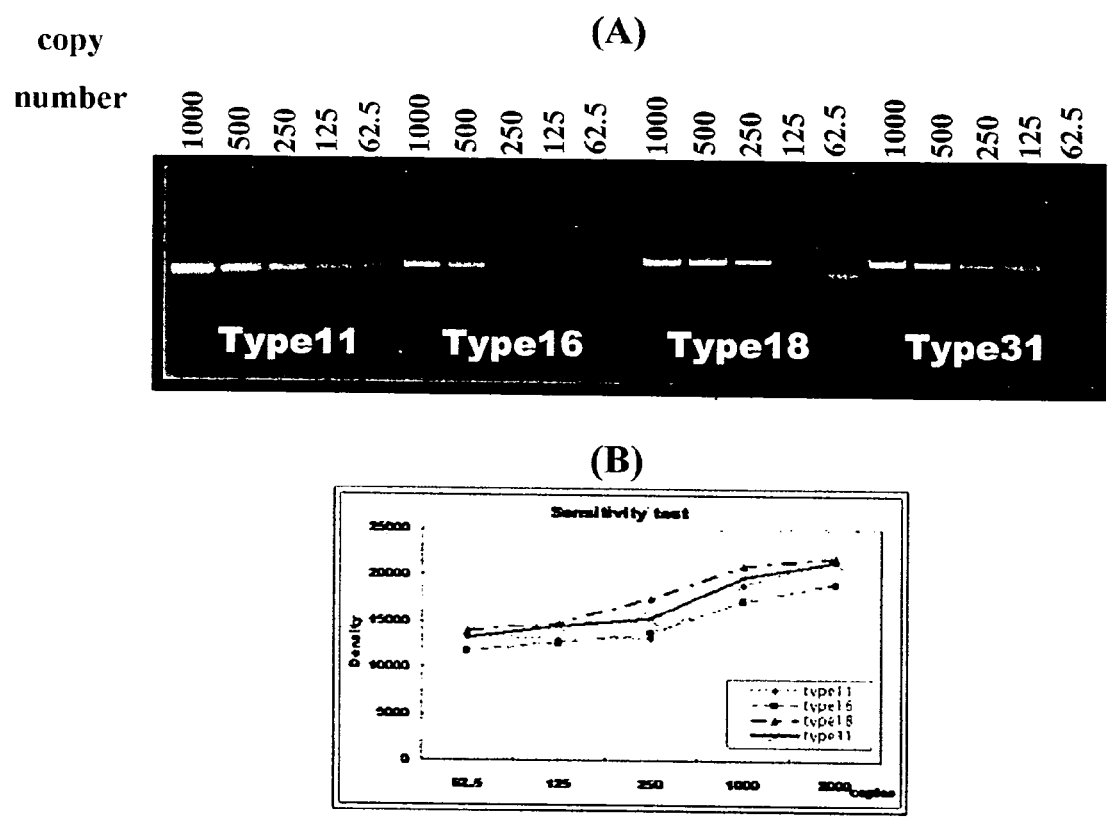
FIG. 7 shows the results of a sensitivity test using plasmid DNA templates, each of which carry the HPV 11, 16, 18 or 31 L1 gene.

PCR was carried out as follows. 5 μl of 2.5 mM dNTP was mixed with 5 μl of 10× buffer, primers (20 pmol) of SEQ ID Nos. 1 to 8, 0.5 μl of Taq polymerase, and distilled water to give a final volume of 40 μl. The mixture was supplemented with 10 μl of each template, thereby yielding a PCR mixture. PCR conditions included 35 cycles of denaturation at 94° C. for 1 min, annealing at 51° C. for 1 min, and extension at 72° C. for 1 min, followed by final extension at 72° C. for 10 min. PCR products were then separated on a 1.5% agarose gel for 40 min, and stained with ethidium bromide (EtBr). Band intensity was measured using the software, Quantity One (Bio-Rad). Then, a regression function was derived in order to determine the relationship between band intensity and the number of plasmid copies, and a relative coefficient R was calculated to determine whether it was greater than 0.9. As a result of the sensitivity test for the PCR amplification method, the band intensity, as shown in FIG. 7, decreased in all of the four HPV genotypes in a manner dependent on the number of plasmid copies, and this PCR method was found to have a sensitivity detecting as few as 62.5 copies of the HPV L1 plasmids. When DNA was run on an agarose gel to determine the relationship between band intensity and the number of plasmid copies, the relative coefficient, as shown in FIG. 7, was greater than 0.9. These results indicate that a plasmid copy number test using the method of the present invention provides reliable results.

EXAMPLE 4

Evaluation of the Specificity of Primers Using the Recombinant HPV L1 Plasmids

Figure 8:
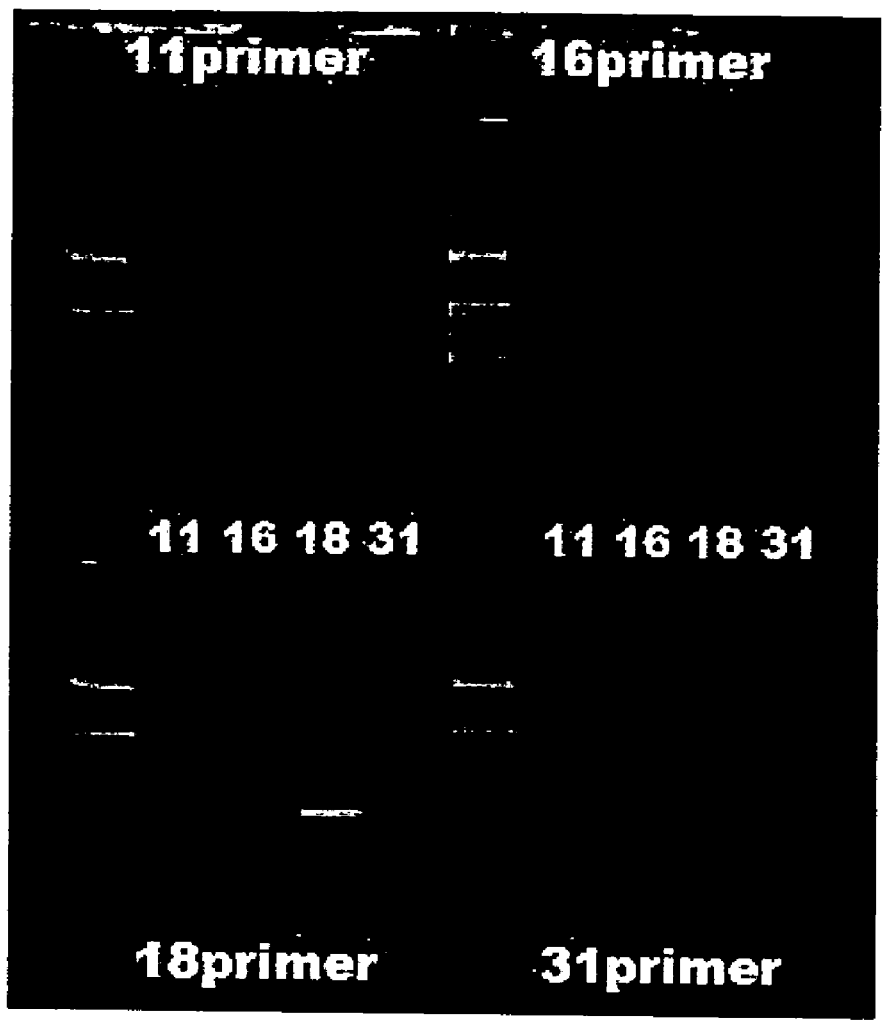
FIG. 8 shows the results of a differentiality test using plasmid DNA templates, each of which carries the HPV 11, 16, 18 or 31 L1 gene.

In order to determine whether the primers used in Example 3 specifically amplify each HPV genotype, the primer sets to the four different HPV genotypes were evaluated for whether they differentially amplify L1 templates of different HPV genotypes. PCR was carried out under the same conditions as in Example 3 except that the templates were used in a concentration of 1000 copies. PCR was performed with each primer set using each of the four different HPV genotypes as a template. As a result of the PCR with each primer set using 1000 copies of each HPV genotype as a template, all primer sets to HPV 11, 16, 18 and 31 were found to specifically amplify only their corresponding templates (FIG. 8). The results, specifically that the primers of the present invention precisely detect only their corresponding HPV genotypes under optimized PCR conditions, indicate that the different primer sets enable HPV genotyping of clinical samples and differential detection of high risk HPV types 11, 16 and 18, infections of which are most likely to progress to cervical cancer. Thus, the present primers may become a very useful means of clinical diagnosis.

EXAMPLE 5

Figure 9:
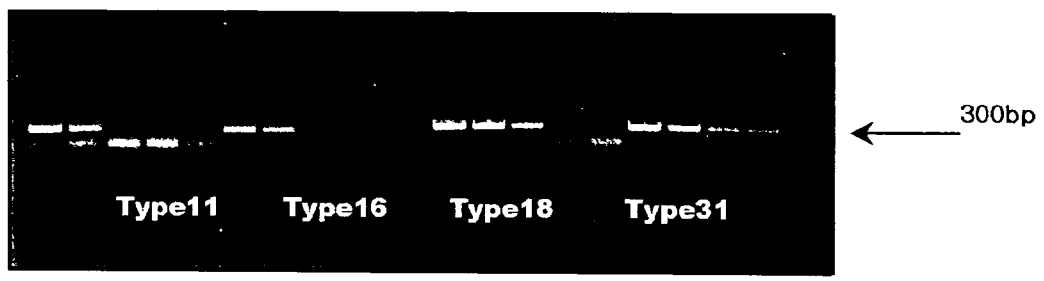
FIG. 9 shows the results of heat stability and long-term preservation tests for HPV L1 plasmids after storage for 3 weeks.
Figure 9:
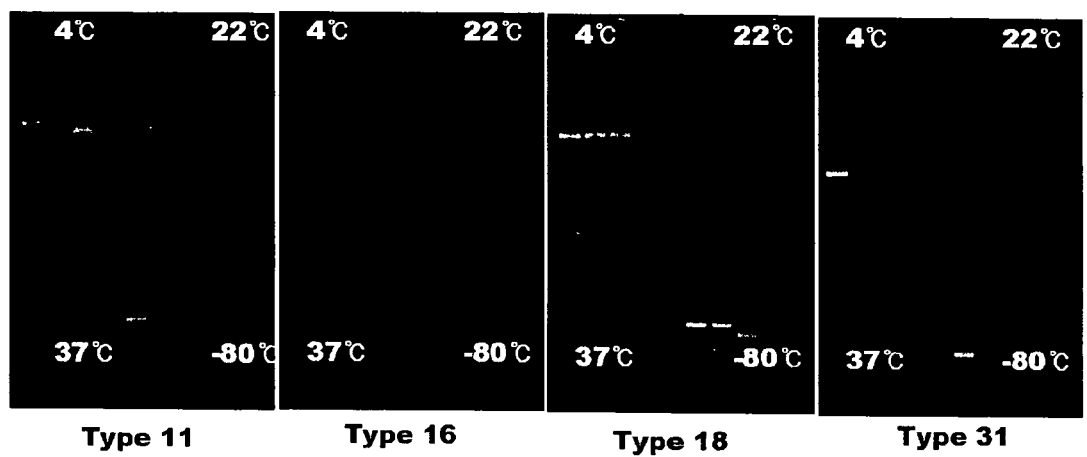
Figure 10:
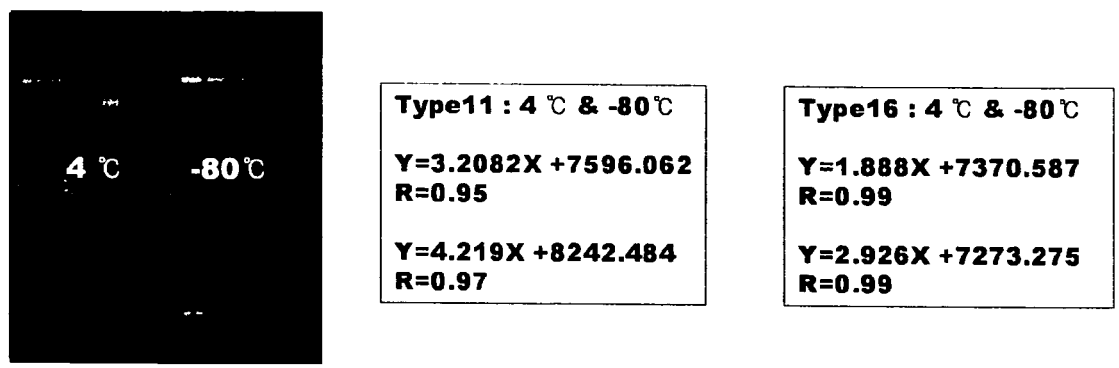
FIGS. 10 and 11 show the results of heat stability and long-term preservation tests for HPV L1 plasmids after storage for 15 weeks.
Figure 10:
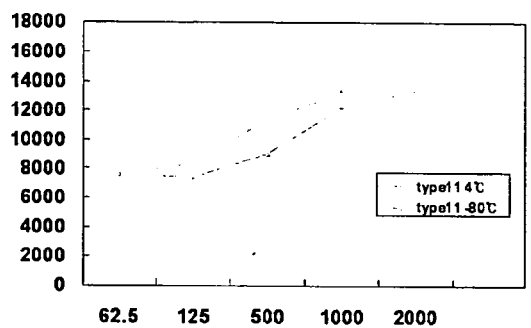
Figure 10:
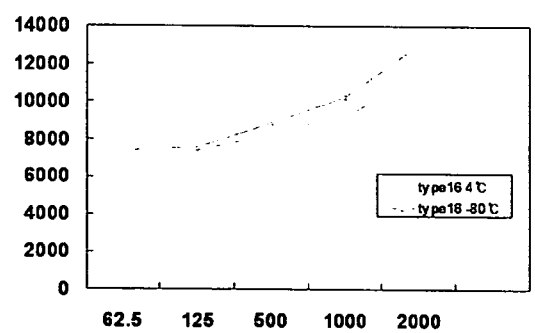
Figure 11:
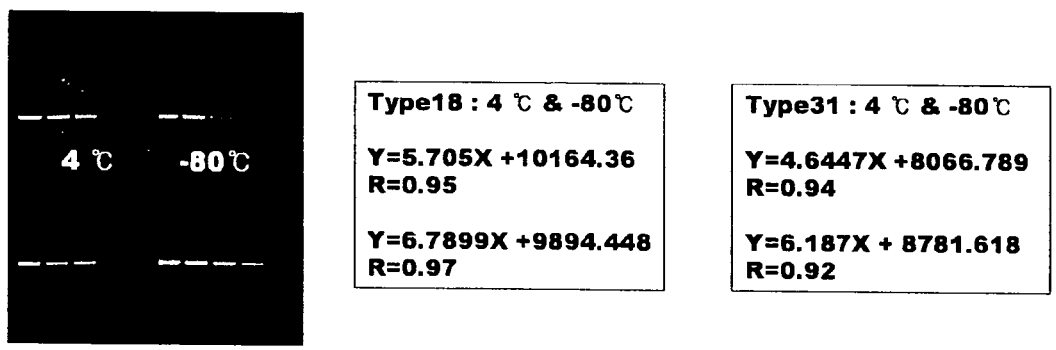
Figure 11:
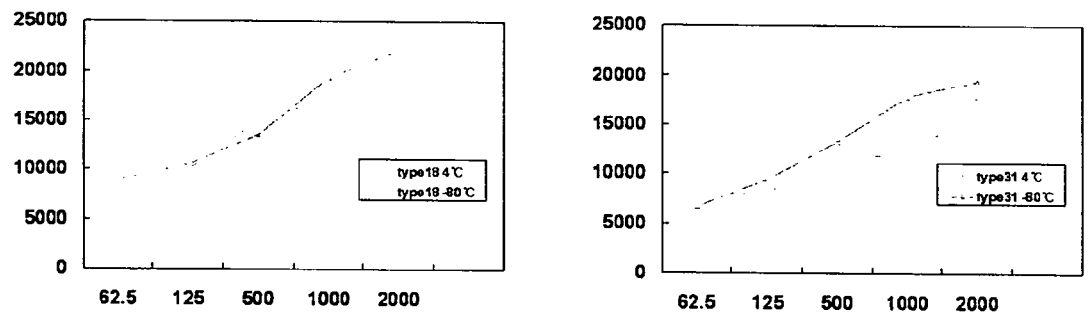

Evaluation of the Heat Stability and Long-Term Preservation of the Recombinant HPV L1 Plasmids To evaluate the heat stability and long-term preservation of primers, first, 30 μl of 1000 copies of each HPV L1 plasmid was aliquotted into fifteen DNase/RNase-free vials. The containers were stored at 4° C., 22° C. and 37° C. for a heat stability test, and at −80° C. for long-term storage. Every three weeks, one vial at each storage temperature was subjected to a sensitivity test, which was carried out according to the same procedure as in Example 3. The PCR with plasmids stored at 22° C. and 37° C. for three weeks showed negative results, indicating that standard DNA has a very low stability when stored at 22° C. and 37° C. (FIG. 9). In contrast, standard DNA stored at 4° C. and −80° C. for 15 weeks still provided highly sensitive PCR results, indicating that the standard DNA of the present invention is stable when stored at −80° C. for a long period of time (FIGS. 10 and 11).

EXAMPLE 6

Figure 12:
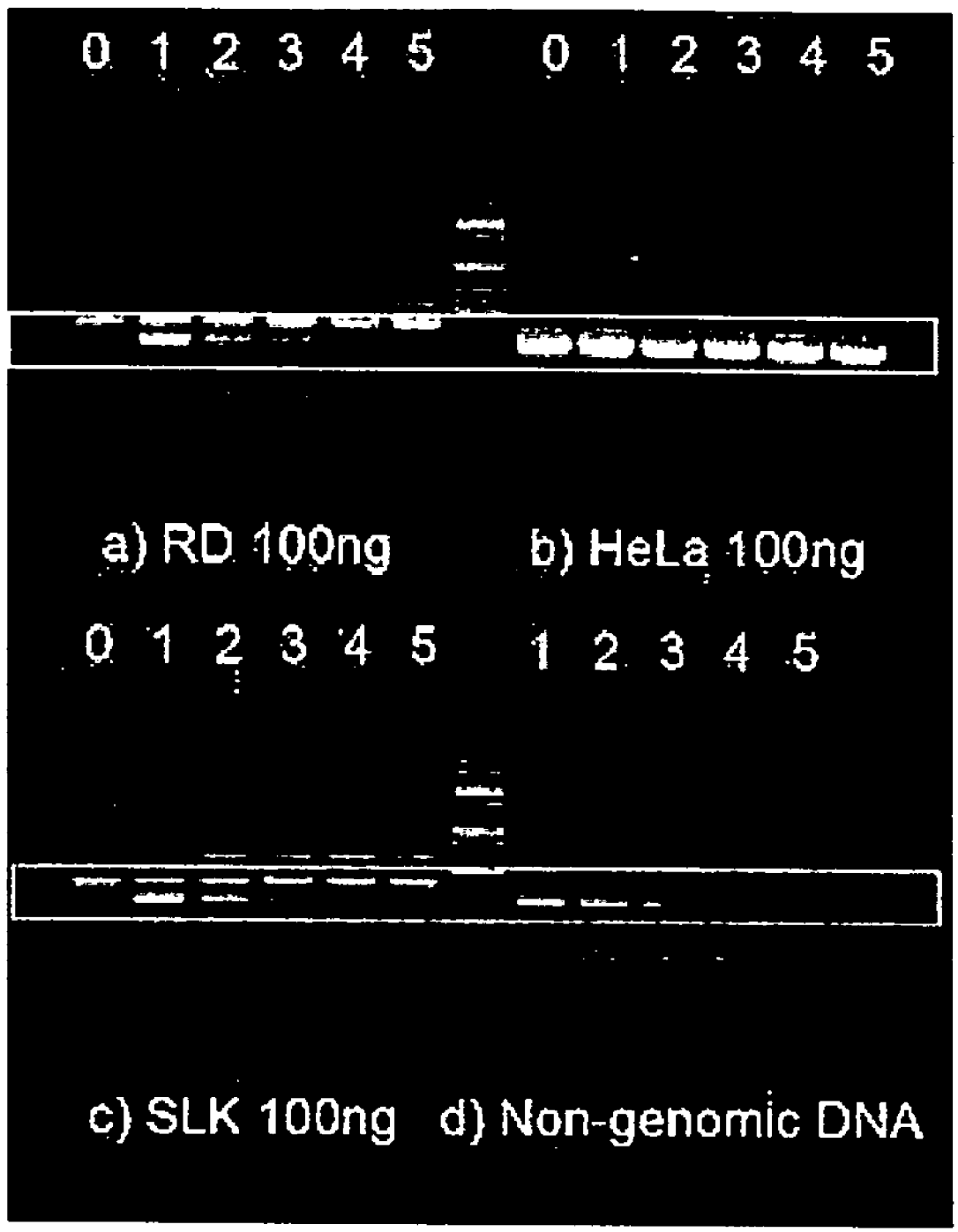
FIG. 12 shows the results of an applicability test using predetermined amounts of HPV L1 plasmids supplemented with various DNA backgrounds.

Evaluation of the Applicability of Primers Using the Recombinant HPV L1 Plasmids The procedure with the HPV L1 templates and primers provided in the present invention was evaluated to determine whether it could detect the HPV genome in human clinical samples, as follows. Genomic DNA was extracted from human rhabdomyosarcoma (RD), HeLa and SLK cells using a genomic DNA extraction kit (Qiagen), and the concentration thereof was determined using a spectrophotometer. Each DNA solution was diluted to concentrations of 10 ng and 100 ng. 100 μl of each dilution was aliquotted and stored at −20° C. Then, PCR was carried out with 100 ng and 1 μg of genomic DNA background using the same templates as in the sensitivity test of Example 3. PCR products were analyzed according to the same method used for the sensitivity test. In the PCR with the genomic DNA background, the HPV templates, as shown in FIG. 12, could be detected even with as few as 62.5 copies, as in the absence of human genomic DNA. The PCR with genomic DNA background from HeLa cells, which contain the HPV 18 genome, exhibited positive results in all lanes.

INDUSTRIAL APPLICABILITY

As described hereinbefore, the primer pairs specific to the L1 gene of HPV 11, 16, 18 and 31 according to the present invention may be useful in the detection of HPV infections, the identification of infected HPV genotypes, evaluation of the effectiveness and toxicity of developed HPV vaccines, and the like.

The invention claimed is:

1. A method of selectively detecting human papillomavirus (HPV) genotypes, comprising performing a polymerase chain reaction for genomic DNA contained in a biological sample using each of the primer pairs having nucleotide sequences represented by SEQ ID Nos. 1 and 2, SEQ ID Nos. 3 and 4, SEQ ID Nos. 5 and 6, and SEQ ID Nos. 7 and 8.

* * * * *

UNITED STATES PATENT AND TRADEMARK OFFICE
CERTIFICATE OF CORRECTION

PATENT NO. : 7,790,375 B2
APPLICATION NO. : 10/581649
DATED : September 7, 2010
INVENTOR(S) : Yang et al.

It is certified that error appears in the above-identified patent and that said Letters Patent is hereby corrected as shown below:

IN THE INVENTION CLAIMED IS:

Col. 13-14 claim 1. "A method of selectively detecting human papillomavirus (HPV) genotypes, comprising performing a polymerase chain reaction for genomic DNA contained in a biological sample each of the primer pairs having nucleotide sequences represented by SEQ ID Nos. 1 and 2, SEQ ID Nos. 3 and 4, SEQ ID Nos. 5 and 6, and SEQ ID Nos. 7 and 8." [[ incorrect ] ]

should read:

1. "A method of selectively detecting human papillomavirus (HPV) genotypes, comprising performing a polymerase chain reaction for genomic DNA contained in a biological sample each of the primer pairs having nucleotide sequences represented by SEQ ID Nos. 1 and 2, SEQ ID Nos. 3 and 4, SEQ ID Nos. 5 and 6, and SEQ ID Nos. 7 and 8, wherein each primer pair binds and specifically amplifies specific regions of the L 1 gene of each of the human papillomavirus (HPV) genotypes HPV 11, HPV 16, HPV 18 and HPV 31." [[ correct ]]

Signed and Sealed this

Twenty-first Day of December, 2010

David J. Kappos
*Director of the United States Patent and Trademark Office*

SEQUENCE LISTING

```
<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: Synthetic

<400> SEQUENCE: 1
ttaggcgttg gtgttagtgg                                                   20

<210> SEQ ID NO 2
<211> LENGTH: 20
<212> TYPE: DNA
<213> ORGANISM: Artificial Sequence
<220> FEATURE:
<223> OTHER INFORMATION: Synthetic

<400> SEQUENCE: 2
aaaattcata gcaccaaagc                                                   20

<210> SEQ ID NO 3
<211> LENGTH: 19
<212> TYPE: DNA
<213> ORGANISM: Artificial Sequence
<220> FEATURE:
<223> OTHER INFORMATION: Synthetic

<400> SEQUENCE: 3
ttaggtgtgg gcattagtg                                                    19

<210> SEQ ID NO 4
<211> LENGTH: 20
<212> TYPE: DNA
<213> ORGANISM: Artificial Sequence
<220> FEATURE:
<223> OTHER INFORMATION: Synthetic

<400> SEQUENCE: 4
aaagtccata gcaccaaagc                                                   20

<210> SEQ ID NO 5
<211> LENGTH: 19
<212> TYPE: DNA
```

<213> ORGANISM: Artificial Sequence
<220> FEATURE:
<223> OTHER INFORMATION: Synthetic

<400> SEQUENCE: 5
ttaggtgttg gccttagtg                                                    19

<210> SEQ ID NO 6
<211> LENGTH: 19
<212> TYPE: DNA
<213> ORGANISM: Artificial Sequence
<220> FEATURE:
<223> OTHER INFORMATION: Synthetic

<400> SEQUENCE: 6
aaagtccatg gcaccatat                                                    19

<210> SEQ ID NO 7
<211> LENGTH: 19
<212> TYPE: DNA
<213> ORGANISM: Artificial Sequence
<220> FEATURE:
<223> OTHER INFORMATION: Synthetic

<400> SEQUENCE: 7
ttaggtgtag gtattagtg                                                    19

<210> SEQ ID NO 8
<211> LENGTH: 19
<212> TYPE: DNA
<213> ORGANISM: Artificial Sequence
<220> FEATURE:
<223> OTHER INFORMATION: Synthetic

<400> SEQUENCE: 8
aaaatccata gctccaaag                                                    19

<210> SEQ ID NO 9
<211> LENGTH: 46
<212> TYPE: DNA
<213> ORGANISM: Artificial Sequence
<220> FEATURE:
<223> OTHER INFORMATION: Synthetic

<400> SEQUENCE: 9
gcccccaagc ttgccgccac catgcaggtg acttttattt acatcc                      46

<210> SEQ ID NO 10
<211> LENGTH: 36
<212> TYPE: DNA
<213> ORGANISM: Artificial Sequence
<220> FEATURE:
<223> OTHER INFORMATION: Synthetic

<400> SEQUENCE: 10
atcgggctcg agcagcttac gttttttgcg tttagc                                 36

<210> SEQ ID NO 11
<211> LENGTH: 39
<212> TYPE: DNA
<213> ORGANISM: Artificial Sequence
<220> FEATURE:
<223> OTHER INFORMATION: Synthetic

<400> SEQUENCE: 11
gcccccaagc ttgccgccac catgtgcctg tatacacgg                              39

```
<210> SEQ ID NO 12
<211> LENGTH: 36
<212> TYPE: DNA
<213> ORGANISM: Artificial Sequence
<220> FEATURE:
<223> OTHER INFORMATION: Synthetic

<400> SEQUENCE: 12
atcggggaat tccttcctgg cacgtacacg cacacg                     36

<210> SEQ ID NO 13
<211> LENGTH: 42
<212> TYPE: DNA
<213> ORGANISM: Artificial Sequence
<220> FEATURE:
<223> OTHER INFORMATION: Synthetic

<400> SEQUENCE: 13
gcccccaagc ttgccgccac catgtctctg tggcggccta gc              42

<210> SEQ ID NO 14
<211> LENGTH: 47
<212> TYPE: DNA
<213> ORGANISM: Artificial Sequence
<220> FEATURE:
<223> OTHER INFORMATION: Synthetic

<400> SEQUENCE: 14
atcggggaat tccttttag ttttttacg ttttgctggt gtagtgg           47

<210> SEQ ID NO 15
<211> LENGTH: 42
<212> TYPE: DNA
<213> ORGANISM: Artificial Sequence
<220> FEATURE:
<223> OTHER INFORMATION: Synthetic

<400> SEQUENCE: 15
gcccccaagc ttgccgccac catgtggcgg cctagcgaca gc              42

<210> SEQ ID NO 16
<211> LENGTH: 42
<212> TYPE: DNA
<213> ORGANISM: Artificial Sequence
<220> FEATURE:
<223> OTHER INFORMATION: Synthetic

<400> SEQUENCE: 16
atcggggaat tcctttttgg ttttggtacg ttttcgtttg gg              42
```